(12) United States Patent
Jadhav et al.

(10) Patent No.: US 7,445,791 B2
(45) Date of Patent: Nov. 4, 2008

(54) SYNERGISTIC INSECTICIDAL COMPOSITION CONTAINING CHLORONICOTYNYLE AND ORGANOPHOSPHORUS COMPOUNDS

(75) Inventors: Prakash Mahadev Jadhav, Maharashtra (IN); Jaidev Rajnikant Shroff, Maharashtra (IN)

(73) Assignee: United Phosphorus, Ltd., Mumbai (IN)

( * ) Notice: Subject to any disclaimer, the term of this patent is extended or adjusted under 35 U.S.C. 154(b) by 228 days.

(21) Appl. No.: 10/888,512

(22) Filed: Jul. 12, 2004

(65) Prior Publication Data

US 2006/0008493 A1    Jan. 12, 2006

(51) Int. Cl.
*A01N 25/12*     (2006.01)
*A01N 57/28*     (2006.01)
*A01N 43/50*     (2006.01)

(52) U.S. Cl. .................. 424/421; 424/405; 424/406; 424/408; 424/409; 424/411; 424/417; 424/418; 424/419; 424/420; 514/119; 514/341

(58) Field of Classification Search .............. None
See application file for complete search history.

(56) References Cited

U.S. PATENT DOCUMENTS

| 5,958,922 | A | | 9/1999 | McAuliffe | |
| 5,983,558 | A | * | 11/1999 | Las et al. | .............. 43/131 |
| 6,264,939 | B1 | | 7/2001 | Light | |
| 6,268,514 | B1 | | 7/2001 | Hamprecht | |
| 6,440,440 | B1 | | 8/2002 | Meerpoel | |
| 6,479,543 | B1 | | 11/2002 | Treacy | |
| 2001/0025050 | A1 | | 9/2001 | Erdelen | |
| 2002/0193352 | A1 | | 12/2002 | Erdelen | |
| 2004/0078843 | A1 | | 4/2004 | Kern | |

FOREIGN PATENT DOCUMENTS

CN    1415205    *    5/2003

* cited by examiner

*Primary Examiner*—Neil Levy
(74) *Attorney, Agent, or Firm*—Jones, Tullar & Cooper, P.C.

(57) ABSTRACT

A synergistic insecticidal composition is prepared by combining a Chloronicotynyle compound and an Organophosphorus (OP) compound. The preferred synergistically effective amount of the Chloronicotynyle compounds is an amount preferably ranging from 0.1 to 5% by weight of the composition. The preferred synergistically effective amount of the Organophosphorus (OP) compounds is an amount preferably ranging from 30 to 75% by weight of the composition. The composition also preferably includes 69.9 to 20% by weight of conventional agriculturally acceptable carrier(s) and/or excipient.

67 Claims, No Drawings

SYNERGISTIC INSECTICIDAL COMPOSITION CONTAINING CHLORONICOTYNYLE AND ORGANOSPHORUS COMPOUNDS

BACKGROUND OF THE INVENTION

1. Field of the Invention

The present invention relates to a synergistic insecticidal composition containing a Chloronicotynyle compound and an Organophosphorus compound and a process thereof for making the composition.

2. Description of Related Art

Enhancement of agricultural produce requires the protection of the crops and its produce from pest damage. Various chemicals and their formulations have been developed and are in use currently for the effective management of insects and pests. Due to non-judicious use of the hitherto known pesticides, the pests have built up a resistance to many pesticides and it has becomes hard to kill them. Physically compatible pesticide mixtures exhibit better pest management. These mixtures show multifaceted advantages than when applied individually, showing a synergistic effect.

The need for more food has to be met through higher yields per unit of land, water, energy and time. Excessive use of mineral fertilizers and chemical pesticides has caused soil degradation, ground water pollution and the spread of the pest's resistant to pesticides in several areas. Hence their judicious use includes avoiding prophylactic sprays, adopting strip treatment, spot application to only those areas with heavy incidence of pests, application to the soil to avoid direct contact with the natural enemies and using selective or non-persistent pesticides. The systemic pesticides are sprayed at a concentration of 0.02 to 0.05 percent active ingredient. The contact pesticides are sprayed at 0.05 to 0.07 or even 0.1 percent active ingredient. The soil application of the granular systemic insecticides varies from 1 to 2 kg a.i./ha. The fungicides are applied up to 2 g/l depending upon the chemical used, pest species and season of the application.

Processes for insecticidal agents and compositions have been developed to control insect pests and in practice have been used as a single or a mixed agent. However, processes for economically efficient and ecologically safe insect control compositions are still being sought. A process for the preparation of insecticidal compositions which allows for reduced effective dosage rates, increased environmental safety and lower incidence of insect resistance are highly desirable. Although the rotational application of insect control agents having different modes of action may be adopted for good pest management practice, this approach does not necessarily give satisfactory insect control. Further, even though combinations of insect control agents have been studied, a high synergistic action has not always been found. Obtaining an insecticidal composition which demonstrates no cross-resistance to existing insecticidal agents, no toxicity problems and little negative impact on the environment is extremely difficult.

Prior U.S. patent applications describe the insecticidal mixtures of Chloronicotynyle compounds with one or more synergistic compound(s) selected from certain specific insecticide compounds. Amongst these synergistic compounds only three compounds belonging to the organophosphorus compounds, namely O,O-dimethyl S-(4-oxo-1,2,3-benzotriazine-3-methyl) dithiophosphate (trade name M-Gusathion); O-ethyl O-(4-bromo-2-chlorophenyl)-s-N-propyl thiophosphate (trade name Curacron); O,S-dimethyl phosphoamidothioate (trade name Tamaron) have been specified to impart synergism. No other compounds falling under this group have been stated. This means that the other compounds falling within the group of organophosphorus compounds have not been demonstrated to provide a synergistic effect when combined with Chloronicotynyle compounds according to the inventions disclosed in prior US patent applications.

Compounds other than organophosphorus compounds which can be combined with Chloronicotynyle compounds consist of 3,5-dimethyl-4-methylthiophenyl N-methylcarbamate [Mesurol]; 4-bromo-2-(4-chlorophenyl)-2-(ethoxymethyl)-5-(trifluoromethyl)-1H-pyrrol-e-3-carbonitrile [AC 303, 630]; N-[2,6-bis(–1-methylethyl)-4-phenoxyphenyl)-N'-(1,1-dimethylethyl)-thiourea [CGA 106 630; Polo]; abamectin; ethyl 3-t-butyl-1-dimethylcar-bam-oyl-1H-1,2,4-triazol-5-ylthio)-acetate [Triazuron]; 6,7,8,9, 10,10-hexachloro-1,5,5A,6,9,9A-hexahydro-6,9-methane-2, 4,3-benzodioxathiepine 3-oxide [Endosulfan; Thiodan]; trans-5-(4-chlorophenyl)-N-cyc-lohexyl-4-methyl-2-oxo-3-thiazolidine-carboxamide [Cesar; Hexythiazox]; 3,6-bis-(2-chlorophenyl)-1,2,4,5-tetrazine [Clofentezin; Apollo]; ethyl [2-(4-phenoxyphenoxy)-ethyl]carbamate [Fenoxycarb; Insegar]; 2-[1-methyl-2-(4-phenoxyphenoxy) ethoxy]pyridine [Pyriproxyfen; Tiger]; N-cyclopropyl-1,3,5-triazine-2,4,6-triamine [Cyromazine]; benzoic acid [-2-benzoyl-1-(1,1-dimethyl)]hydrazide [RH 5849]; 5-amino-3-cyano-1-(2,6-dichloro-4-trifluoromethylphenyl)-4-trifluoromethylthionopyrazole [Fipronil]; cis-(2,3,5,6-tetrafluoro-4-methylphenyl)methyl-3-(2-chloro-3,-3,3-trifluoro-1-propenyl)-2,2-dimethyl-cyclopropane-carboxylate [Tefluthrin; Force]; 1,5-bis-(2,4-dimethylphenyl)-3-methyl-1,3,5-triazape-nta-1,4-dione [Amitraz]; 3,5-dimethylbenzoic acid 1-(1,1-dimethylethyl)-2-(4-ethylbenzoyl)hydrazide [RH 5992]; N-[[2,5-dichloro-4-(1,1,2,3,3,3-hexafluoropropoxy) phenyl]-aminocarbonyl]-2,6-difluorobenzamide [Match]; (4-ethoxyphenyl)-[3-(4-fluoro-3-phenoxyphenyl) propyl] dimethylsilane [HOE 498]; and (E)-4,5-dihydro-6-methyl-4-[(3-pyridinylmethylene) amino]-1,2,4-triazin-3-(2H)-one [Chess].

Most of the above mentioned compounds employed in the composition resulting in synergism are all earlier generation insecticides having high toxicity. Many of these compounds are currently restricted and/or banned for use in certain countries due to their toxicity. Therefore, though the compositions disclosed above have synergistic activity, their practical application for use is either limited or banned The invention disclosed in prior US applications does not disclose the use of any other advanced and safer organophosphorus insecticide such as Acephate, Phosphamidon, Chlorpyrifos Azarnethiphos, Azinphos-ethyl, Azinphos-methyl, Cadusafos, Chlorethoxyfos, Chlorfenvinphos, Chlormephos, Chlorpyrifos, Chlorpyrifos-methyl, Cumaphos, Cyanophos, Demeton-5-methyl, Diazinon, Dichlorvos, Dicrotophos, Dimethoate, Dimethylvinphos, Dioxabenzofos, Disulfoton, Ethion, Ethoprophos, Famphur, Fenitrothion, Fenthion, Fonofos, Formothion Heptenophos, Isazofos, Isofenphos, Isoxathion, Malathion, Mecarbam, Mephosfolan, Methidathion, Mevinphos, Monocrotophos, Naled, Omethoate, Oxydemeton-methyl, Parathion, Parathion-methyl, Phenthoate, Phorate, Phosalone, Phosmet, Phosphamidon, Phoxim, Primiphos-ethyl, Primiphos-methyl, Profenofos, Propaphos, Propetamphos, Prothiofos, Pyraclofos, Quinalphos, Sulfotep, Sulrpofos, Temephos, Terbufos, Tetrachlorvinphos, Thiometon, Triazophos, Vamidothion. This means that there does not appear to be any known advanced and safer organophosphorus compounds having synergistic effect when combined with Chloronicotynyle compounds.

In addition, the invention disclosed in the prior US applications describes only the effect of using two insecticidal compounds as an admixture in a tank-mix form at the time of the application on crops. In other words the ingredients have to be mixed as and when required at the place of application. In short, the inventions disclosed in the prior patent applications do not result in a compatible and storage stable formulation product, prepared in the manufacturing plant and made available to use in a packed container on a shelf. It also does not disclose the specific concentrations or concentration range of the compound that exhibits synergistic effects. This means that if the ingredients are mixed in advance and kept, their activity may either be reduced or totally lost. Thus, the composition cannot be prepared as a ready-to-use composition.

Thus, there is need to develop and improve insecticidal composition for a variety of reasons including: 1) to increase agricultural yield; 2) to provide a composition having high synergistic action; 3) to provide a composition having no cross resistance to existing insecticidal agents; 4) to avoid excess loading of the toxicant to the environment; and 5) to negligibly impact environmental safety. A need also exists for synergistic insecticidal compositions which could be physico-compatible formulations in the form of storage stable, safely packed, ready-to-use formulation.

BRIEF SUMMARY OF THE INVENTION

The present invention achieves the above objectives by providing a synergistic insecticidal composition containing a Chloronicotynyle compound and an Organophosphorus compound. The present invention is also directed to a process for making the synergistic insecticidal composition containing the Chloronicotynyle compound and the Organophosphorus compound.

The synergistic insecticidal composition containing the Chloronicotynyle compound and the Organophosphorus compound has a variety of advantages including those provided herein. The synergistic insecticidal composition demonstrates a high controlling effect with reduced crop protection cost, increased crop yield and reduced environmental load. The synergistic insecticidal composition prepared by the process of the present invention is especially useful for the control of agricultural pests and hygienic pests. The synergistic insecticidal composition is highly effective for the protection of growing plants including: cotton, paddy, rice forage crops, sugarcane, cole crops, leafy vegetables, tobacco, tomatoes, potatoes, flowering ornamentals, vine crops and fruit trees from the ravages of insects. The synergistic insecticidal composition is found to be highly active against a wide variety of chewing, boring and sucking insects, e.g. Aphids, thrips, lepidopterous larvae, sawflies, leafminers, leafhoppers, cutworms, whiteflies, soil insects, termites and some species of biting insects, such as rice water weevil or Colarado beetle. The synergistic insecticidal composition is also useful for synergistic insect control and enhanced crop protection and delays the dominance of the resistant strains of pests. The synergistic insecticidal composition also has a broader spectrum of activity and reduces risk of developing resistance than other insecticidal compositions. Another benefit of the synergistic insecticidal composition is that it can achieve effective and economic control of undesirable species. Yet another advantage of the present synergistic insecticidal composition is that it can improve biological performance in a single application and minimize occupational exposure and hazards. Still another advantage of the present invention is to provide a synergistic insecticidal composition which decreases the cost of application, saves fuel cost, labor cost and saves applicator's precious time and is therefore very economical. Additionally, the present invention provides a synergistic insecticidal composition which reduces the wear of equipment and losses caused by mechanical damage to crops and soil.

DETAILED DESCRIPTION OF THE INVENTION

The present invention provides a process for preparing a synergistic insecticidal composition containing a Chloronicotynyle compound and an Organophosphorus compound. A synergistically effective amount of one or more compounds falling within a group of Chloronicotynyle compounds is an amount preferably ranging from 0.1 to 5% by weight of the composition, more preferably in the range of 0.5 to 3.0% of Chloronicotynyle compounds. The Chloronicotynyle compounds are preferably selected from the group consisting of Imidacloprid and Acetamiprid, most preferably Imidacloprid, which may be Technical grade and provided in a purity of 95% minimum. The Chloronicotynyle compound is provided in combination with one or more Organophosphorus compounds present in an amount preferably ranging from 30 to 75% by weight of the composition, more preferably 35 to 60% by weight Organosphosphorus compounds. The compounds falling under the group of Organophosphorus compounds are preferably selected from the group consisting of Acephate and Phosphamidon, more preferably Technical grade Acephate having a purity of 97% minimum and Technical grade Phosphamidon having a purity of 92% minimum. The synergistic insecticidal composition also preferably includes 69.9 to 20% by weight of conventional agriculturally acceptable carrier(s) and/or excipients.

The amount of the Organophosphorus compound, except Azinphos-methyl, Profenofos and Methamidophos, used in the process may be preferably selected from the group consisting of Acephate, Azamethiphos, Azinphos-ethyl, Cadusafos, Chlorethoxyfos, Chlorfenvinphos, Chlormephos, Chlorpyrifos, Chlorpyrifos-methyl, Cumaphos, Cyanophos, Demeton-5-methyl, Diazinon, Dichlorvos, Dicrotophos, Dimethoate, Dimethylvinphos, Dioxabenzofos, Disulfoton, Ethion, Ethoprophos, Famphur, Fenitrothion, Fenthion, Fonofos, Formothion, Heptenophos, Isazofos, Isofenphos, Isoxathion, Malathion, Mecarbam, Mephosfolan, Methidathion, Mevinphos, Monocrotophos, Naled, Omethoate, Oxydemeton-methyl, Parathion, Parathion-methyl, Phenthoate, Phorate, Phosalone, Phosmet, Phosphamidon, Phoxim, Primiphos-ethyl, Primiphos-methyl, Propaphos, Propetamphos, Prothiofos, Pyraclofos, Quinalphos, Sulfotep, Sulrpofos, Temephos, Terbufos, Tetrachlorvinphos, Thiometon, Triazophos, Vamidothion. The more preferred Organophosphorus compound is Acephate and Phosphamidon and their mixtures. The amount of Organophosphorus compound present may vary accordingly to prevailing conditions such as the particular Organophosphorus compound present, insect pest attack strength, type of pests, application timing, weather conditions, soil conditions, mode of application, topographical character, target crop and the like.

An agriculturally acceptable carrier may be solid, liquid or both. Solid carries are essentially: mineral earth such as silicas, silica gels, silicates, talc, kaolin, montmorillonite, attapulgite, pumice, sepiolite, bentonite, limestone, lime, chalk, bole, loes, clay, dolomite, diatomaceous earth, calcite, calcium sulfate, magnesium sulfate, magnesium sulfate, magnesium oxide, sand, ground plastics, ferilizers such as ammonium sulfate, ammonium phosphate, ammonium nitrate, ureas, and crushed products of vegetable origin such as cereal meal, tree bark meal, wood meal and nutshell meal, cellulose powders, or other solid carriers.

The synergistic insecticidal composition may optionally include surfactant(s) which are non-ionic, cationic and/or anionic in nature and surfactant mixtures which have good emulsifying, dispersing and wetting properties, depending on the nature of the active ingredient to be formulated. Suitable anionic surfactants can be both so-called water-soluble soaps and water-soluble synthetic surface-active compounds. Soaps which may be included as a surfactant are the alkali metal, alkaline earth metal or substituted or unsubstituted ammonium salts of higher fatty acids ($C_{10}$-$C_{22}$), for example the sodium or potassium salt of oleic or stearic acid, or of natural fatty acid mixtures.

According to the present invention there is provided a process for preparing a synergistic insecticidal composition which comprises mixing thoroughly, one or more Chloronicotynyle compounds in an amount ranging from 0.1 to 5% by weight of the composition, more preferably in the range of 0.5 to 3.0% of Chloronicotynyle compounds one or more Organophosphorus compounds, except Azinphos-methyl, Profenofos and Methamidophos, in an amount ranging from 30 to 75% by weight of the composition, more preferably 35 to 60% of Organophsophorus compounds, and 69.9 to 20% by weight of the composition conventional agriculturally acceptable excipient(s) and or carrier(s). The Chloronicotynyle compound is preferably Imidacloprid and/or Acetamiprid, preferably Imidacloprid, which may be Technical grade and purity of 95% minimum. The Organophosphorus compound, except Azinphos-methyl, Profenofos and Methamidophos, is preferably selected from Acephate and/or Phosphamidon, most preferably Acephate having a purity of 97% minimum and Phosphamidon having a purity of 92% minimum. Other preferred Organophosphorus compounds have been listed previously in connection with the synergistic insecticidal composition and may be used in the present process.

The process of this invention includes intensive mixing and/or milling of the Chloronicotynyle compound and the Organophosphorus compound (referred to as active ingredients) with other optional substances, such as a stabilizer, an emetic agent, a disintegrating agent, an antifoaming agent, a wetting agent, a dispersing agent, a binding agent, dye(s), fillers, carriers, surface active compounds (surfactants), and optionally solid and/or liquid auxiliaries and/or adjuvants such as wetters, adhesives, dispersants or emulsifiers.

The name "Acetamiprid" describes a chemical substance having a molecular weight 222.7; is in the form of colourless crystals, m.pt. 98.9° C.; solubility in water at 25° C., 4200 mg/l. Soluble in acetone, methanol, ethanol, dichloromethane, chloroform, acetonitrile and tetrahydrofuron. Stable in buffered solutions at pH 4,5,7. Degraded slowly at pH 9 and 45° C. Stable under sunlight. The molecule have following formula:

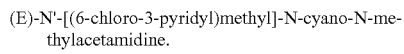

(E)-N'-[(6-chloro-3-pyridyl)methyl]-N-cyano-N-methylacetamidine.

It is a systemic insecticide for soil and foliar application. Controls Hemiptera, especially aphids, Thysanoptera and Lepidoptera on wide range of crops, especially vegetables, fruits and tea. Its acute oral LD50 for male rats 217, female rats 146, male mice 198, female mice 184 mg/Kg. Acute percutaneous LD50 for male and female rats>2000 mg/Kg. Non irritating to skin and eyes (rabbits) During inhalation LC50 (4 h) for male and female rats is about>0.29 mg/l.

The name "Imidacloprid" describes a chemical substance having a molecular weight 255.7; is in the form of colourless crystals with a weak characteristic odour, m.pt. 144° C.; solubility in water at 20° C., 0.61 g/l. In dichloromethane 55, isopropanol 1.2, toluene 0.68, n.hexane<0.1 (all in g/l. 20° C.). Stable to hydrolysis at pH 5-11. The molecule have following formula:

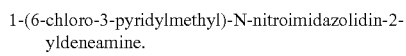

1-(6-chloro-3-pyridylmethyl)-N-nitroimidazolidin-2-yldeneamine.

It acts on the central nervous system, causing blockage of postsynaptic nicotinergic acetylcholine receptors. It is a systemic insecticide with contact and stomach action. Readily taken up by the plant and further distributed acropetally, with good root-systemic action. It controls the sucking insects, including rice-hoppers, aphids, thrips and whiteflies. Also effective against soil insects, termites and some species of biting insects, such as rice water weevil and Colorado beetle. It has no effect on nematodes and spider mites. Used as seed dressing, as soil treatment and as foliar treatment in different crops, e.g. rice, cotton, cereals maize sugar beet, potatoes, vegetables citrus fruit, pome fruit and stone fruit. Its acute oral LD50 for male and female rats 450, mice 150 mg/Kg. Acute percutaneous LD50 (24 h) for rats>5000 mg/Kg. Non irritating to skin and eyes (rabbits). Not a skin sensitiser. During inhalation LC50 (4 h) for female rats is>5323 mg/m$^3$ air (aerosol). Not mutagenic or teratogenic.

Descriptions of the above-listed commercially available compounds may be found in "The Pesticide Manual" 11$^{th}$ Edition, British Crop Protection Council (1997) among other publications.

The Organophosphorus compounds have high insecticidal and acaricidal activity; have wide spectrum of the action on plant pests; low persistence and breakdown to form products nontoxic to human and animals; systemic action of a number of the compounds; low dosage of the compound per unit area treated; relatively rapid metabolism in vertebrate organism and absence of accumulation in their bodies, and also comparatively low chronic toxicity; rapidity of action on plant pests. The preferred compounds for use as Organophosphorus compounds are Acephate and Phosphamidon.

"Acephate" (O,S-dimethylacetylphosphoramidothioate) belongs to Organophosphorus group and has the structural formula as follows:

(O,S-dimethylacetylphosphoramidothioate)

It is a cholinesterase inhibitor. It is a systemic insecticide with contact and stomach action and is of moderate persistence with residual activity lasting about 10-21 days. It controls a wide range of chewing and sucking insects, e.g. aphids, thrips, lepidopterous larvae, sawflies, leaf miners, leafhoppers, cutworms, etc. in fruits (including citrus), vines, hops, olives, cotton soyabean, peanuts, macadamia nuts, beet, brassicas, celery, beans, potatoes, rice, tobacco ornamentals, forestry, and other crops. It is non-phytotoxic to most crop plants but marginal leaf burn may occur on Red Delicious apples. Technical grade Acephate is>97% pure. It has a molecular weight of 183.2 is a colourless solid; melting point 88-90° C.; solubility at room temperature: about 790 g/l water (20 C); 151 acetone, >100 ethanol; 35 ethyl acetate, 16 benzene, 0.1 hexane (all in g/l, 20° C.). Relatively stable to hydrolysis; DT50 40° C. 60 h (pH 9), 710 h (pH 3).

The "Phosphamidon" as a commercial compound contains 70% m/m (Z)-isomer (β-isomer) (which has the greater insecticidal activity) and 30% m/m (E)-isomer (α-isomer). Phosphamidon is a systemic insecticide and acaricide with stomach and slight contact action. It is a pale yellow liquid with the molecular structure as follows:

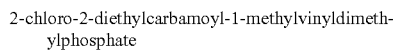

2-chloro-2-diethylcarbamoyl-1-methylvinyldimethylphosphate

It is absorbed by the leaves and roots. It is cholinesterase inhibitor. It is used in control of sucking, chewing and boring insects, and spider mites on a very wide range of crops. Specifically used in control of leaf beetles and stem borers in rice; stem borers in sugarcane; colarado beetles in potatoes; thrips in cotton; etc. It is also used to control aphids, sawflies, suckers, fruit flies, leaf miners, moth and beetle larvae, and many other insects in fruits, vines, olives, vegetables, ornamentals, cereals, beet, maize, alfalfa, many other crops and in forestry. It is non-phytotoxic, except some varieties of cherry, plum, peach and sorghum. It is compatible with many other pesticides, but incompatible with alkaline materials. It has a boiling point 162° C. (at 1.5 mm Hg); Solubility-miscible with water, acetone, dichloromethane, toluene and other common organic solvents, with the exception of aliphatic hydrocarbons e.g. solubility in hexane 32 g/l (25° C.). It gets rapidly hydrolysed in alkali: DT 50 (calculated) (20° C.) 60 d (pH 5); 54 d (pH 7); 12 d (pH 9). Its acute oral LD 50 for rats 17.9-30 mg/Kg. Acute percutaneous LD 50 for rats 374-530, rabbits 267 mg/Kg. Slight skin irritation, moderate eye irritation in rabbits observed. During inhalation LC 50 (4 h) for rats is about 0.18, mice 0.033 mg/l air. In mammals, following oral administration, 85-90% of the dose is excreted within 24 hours, almost entirely in the urine. Complete metabolism occurs during the passage, by oxidative dealkylation of the amide group and hydrolysis of the phosphorus ester bond. In plants, an ethyl group is split off from the amide group and simultaneously or subsequently the ester bond between the side chain and phosphorus atom is hydrolytically cleaved. De-chlorination also occurs, as does further degradation to small fragments.

Pesticidal compositions are often formulated and transported in a concentrated form which is subsequently diluted by the user before application. The presence of small amounts of a surfactant facilitates this process of dilution. Thus, preferably a composition according to the present invention comprises, if desired, at least one surfactant. For example, the composition may contain one or more carriers and at least one surfactant.

A carrier in a composition according to the present invention is any material with which the active ingredient is formulated to facilitate application to the locus to be treated, which may for example be a plant, seed or soil, or to facilitate storage, transport or handling. A carrier may be a solid or a liquid, including material which is normally a gas but which has been compressed to form a liquid or a combination thereof. The composition of the present invention may also contain other additive such as surfactants, emulsifiers, defoamers, buffers, thickeners, dyes, extenders, emetic agent (s) and the like.

Surprisingly, it has been found that the synergistic insecticidal composition prepared by the process of the present invention has superior insect control at lower levels of the combined concentrations of the Chloronicotynyle compound and Organophosphorus compound (also referred to as the "active ingredients") employed than that may be achieved when the Chloronicotynyle compound and Organophosphorus compound are applied alone. In other words, the process of preparing the synergistic insecticidal composition of the present invention and the composition resulting therefrom, is not a mere admixture of the active ingredients resulting in the aggregation of the properties of the active ingredients employed in the composition. The process involves judicial selection of the appropriate amounts of the active ingredients which combination only imparts synergism to the resulting composition imparting to it the unexpected and unique properties.

Advantageously, known adjuvants which are known to enhance the activity, may also be incorporated in the process of preparing the synergistic insecticidal composition. The synergistic insecticidal composition resulting from the process may be dispersed in a solid or liquid diluent for application to the insect, its food supply, breeding ground or habitat as a dilute spray or as a solid dust or dust concentrate.

As a commodity the synergistic insecticidal composition is generally in a ready to use form which may be diluted at the place of application for suitable concentration of the active ingredients.

In general, the synergistic effect may be achieved at application rates of the active ingredient of about 20 to 25 g/ha of Imidacloprid in combination with 250 to 750 g/ha of Acephate; preferably in about 1 to 1500 g/ha. In general, the synergistic effect may be achieved at application rates of the active ingredient of about 20 to 25 g/ha of Imidacloprid in combination with 0.03 to 600 g/ha of Phosphamidon; preferably in about 0.5 to 750 g/ha.

Preferred combinations of the synergistic insecticidal composition prepared by the process of the present invention are those combination wherein the active ingredient ratio (weight/weight) of Chloronicotynyle:Organophosphorus compound is about 1:1 to 1:1000. More preferred combination of the invention are combination of Chloronicotynyle (Imidacloprid) and Organophosphorus (Acephate) wherein the active ingredient ratio (weight/weight) of Imidacloprid: Acephate is about 1:2 to 1:800, most preferred is about 1:5 to 1:800. More preferred combination of the invention are combination of Chloronicotynyle (Imidacloprid) and Organophosphorus (Phosphamidon) wherein the active ingredient ratio (weight/weight) of Imidacloprid:Phosphamidon is about 1:2 to 1:800, most preferred is about 1:5 to 1:800

Advantageously, the Chloronicotynyle compound or a mixture thereof may be formulated with a second insecticidally effective ingredient alone or a mixture thereof and optionally other agriculturally acceptable carrier and formulation adjuvants. Said formulation may be dispersed in a solid or liquid diluent for application to the insect, its food supply, breeding ground or habitat as a dilute spray or as a solid dust or dust concentrate.

As a commodity the synergistic insecticidal compositions may preferably be in a concentrated form (i.e. 30.1 to 80%) whereas the end user generally employs diluted compositions. The synergistic insecticidal composition may be diluted to a concentration down to 0.001% of active ingredient. Preferably, the formulation comprise approximately from 30.1 to 80% by weight, of active ingredients. The doses usually are in the range from 0.01 to 10 kg a.i./ha. The ratio of the essential active ingredients of the synergistic insecticidal composition of the invention is about 0.1-5.0 weight part of Imidacloprid to about 30-75 weight parts of one or more compounds selected from Organophosphorus group, except Azinphos-methyl, Profenofos and Methamidophos.

Advantageously, the synergistic insecticidal composition of the invention may be formulated in powder, solid or liquid form. A preferred powder form comprises a synergistically effective amount of a combination of the Chloronicotynyle compound plus one or more compounds selected from a group of Organophosphorus compounds, except Azinphos-methyl, Profenofos and Methamidophos, and solid or liquid inert substance(s).

A preferred soluble powder composition may contain by weight about 30.1% to 80% active ingredients preferably Imidacloprid in combination with Acephate and or Phosphamidon.

The forms of application of the synergistic insecticidal compositions according to this invention depend on the intended purposes; in any case, they guarantee a uniform distribution of the active ingredients. They can be applied, for example, in the form of directly sprayable aqueous solutions, powders, suspensions, also highly-concentrated aqueous suspensions or dispersions, dusts, materials for spreading or granules, by spraying, atomizing, dusting or pouring. Aqueous use forms can be prepared from soluble powders (SP) by adding water.

Alternatively, synergistic insecticidal compositions which consist of insecticidally active ingredients, wetter, adhesive, dispersant or surfactants and, if appropriate solvent or oil may be prepared, and such synergistic insecticidal compositions are suitable for dilution with water.

Aqueous dispersions and suspensions, for example synergistic insecticidal compositions obtained by diluting the formulated product according to the invention with water, also lie within the scope of the invention.

The biological activity of the active ingredient can also be increased by including an adjuvant in the spray dilution. An adjuvant is defined herein as a substance which can increase the biological activity of an active ingredient but is not itself significantly biologically active. The adjuvant can either be included in the synergistic insecticidal composition as a co-formulant or carrier, or can be added to the spray tank together with the synergistic insecticidal composition containing the active ingredient.

In actual practice, the composition of the invention may be applied to the plant foliage or plant stem or to the insect habitat or to the locus of a hygienic pest as a dilute spray prepared from any of the above-said formulations.

The synergistic effective amount of the combination of the preferred Imidacloprid and Organophosphorus compound selected from Acephate, Phosphamidon, Chlorpyrifos, Dichlorvous, Monocrotophos, Quinalphos and others may vary accordingly to prevailing conditions such as the particular Organophosphorus compound present, insect pest attack strength, type of pests, application timing, weather conditions, soil conditions, mode of application, topographical character, target crop and the like.

The synergistic insecticidal composition prepared by the process of the present invention is a superior insecticidal composition and is especially useful for the control of agricultural pests, hygienic pests. Said synergistic insecticidal compositions are highly effective for the protection of growing plants including: cotton, paddy, rice forage crops, sugarcane, cole crops, leafy vegetables, tobacco, tomatoes, potatoes, flowering ornamentals, vine crops and fruit trees from the ravages of insects.

The synergistic insecticidal composition prepared by the process of the invention is found to be highly active against a wide variety of chewing, boring and sucking insects, e.g. Aphids, thrips, lepidopterous larvae, sawflies, leafminers, leafhoppers, cutworms, whiteflies, soil insects, termites and some species of bitting insects, such as rice water weevil on Colarado beetle etc.

The present invention highlights the synergistic effect of the combination of the Chloronicotynyle compound and Organophosphorus compound. Following the right use of the invented technology and the synergistic insecticidal composition of the invention with a formulations having a multi-pesticide components i.e. pesticide mixture, formulation prepared with an extra care of physical compatibility by purposefully specially selected solvents, carriers and the surfactants, thickeners, stabilisers etc. exhibits better pest management.

These and other advantages of the invention may become more apparent from the examples set forth herein below. These examples are provided merely as illustrations of the invention and are not intended to be construed as a limitation thereof.

EXAMPLE-1

Preparation of a Synergistic Insecticidal Composition Containing Imidacloprid 1.8%+Acephate 50% [51.8% SP]:

Composition

| Ingredient | Quantity (% w/w) |
| --- | --- |
| Imidacloprid Techical (purity 95%) | 1.8948 |
| Acephate Technical (purity 97%) | 51.5465 |
| Stabilizer (Sodium alginate) | 3.0000 |
| Emetic agent (Bitrex) | 0.0002 |
| Disintegrating agent (Zeolite) | 5.0000 |
| Antifoaming agent (Antimousse 426-R) | 0.1000 |
| Wetting cum dispersing agent (Lisapol BN-200) | 1.5000 |
| Anticaking agent (anhydrous Magnesium sulphate) | 0.0100 |
| Dye(s) | 0.0010 |
| Fillers (s) (Insilco and Kaolex) | 36.9475 |
| Total | 100.00% (w/w) |

Process for the preparation of the above said synergistic insecticidal composition comprises mixing thoroughly, for ½ hour, Imidacloprid, antimousse 426-R, Lisapol BN-200, anhydrous Magnesium sulphate, Insilco, Kaolex, Acephate, sodium alginate, Bitrex, Zeolite, and Ocean blue in a pre-blender equipped with an agitator to get a homogenous mixture of all the ingredients. Thereafter, the homogenous mixture obtained is micronised to get a particle size of 2-10 microns which is post-blended to yield the synergistic insecticidal composition

EXAMPLE-2

Preparation of a Synergistic Insecticidal Composition Containing Imidacloprid 2.0%+Acephate 45.0% [47% SP]:

Composition

| Ingredient | Quantity (% w/w) |
| --- | --- |
| Imidacloprid Techical (purity 95%) | 2.1053 |
| Acephate Technical (purity 97%) | 46.3918 |
| Stabilizer (Sodium alginate) | 2.7500 |
| Emetic agent (Bitrex) | 0.0002 |
| Disintegrating agent (Zeolite) | 5.3000 |
| Antifoaming agent (Antimousse 426-R) | 0.1000 |
| Wetting cum dispersing agent (Lisapol BN-200) | 1.5000 |
| Anticaking agent (anhydrous Magnesium sulphate) | 0.0100 |
| Dye(s) (Malachite green) | 0.0010 |
| Fillers (s) (Insilco and Kaolex) | 41.8417 |
| Total | 100.00% (w/w) |

The process of preparing the above composition comprises mixing thoroughly, for ½ hour, Imidacloprid, antimousse 426-R, Lisapol BN-200, anhydrous Magnesium sulphate, Insilco, Kaolex, Acephate, sodium alginate, Bitrex, Zeolite and malachite green in the above mentioned proportions in a pre-blender equipped with an agitator to get a homogenous mixture of all the ingredients. Thereafter, the homogenous mixture obtained is micronised to get a particle size of 2-10 microns which is post-blended to yield the synergistic insecticidal composition.

EXAMPLE-3

Process for the Preparation of a Synergistic Insecticidal Composition Containing Imidacloprid 3.0%+Acephate 40.0% [43% SP]:

Composition

| Ingredient | Quantity (% w/w) |
| --- | --- |
| Imidacloprid Techical (purity 95%) | 3.1579 |
| Acephate Technical (purity 97%) | 41.2372 |
| Stabilizer (Magnesium stearate) | 3.5000 |
| Emetic agent (Bitrex) | 0.0003 |
| Disintegrating agent (Zeolite) | 6.0000 |
| Antifoaming agent (Antimousse 426-R) | 0.0500 |
| Wetting cum dispersing agent (Lisapol-D) | 2.0000 |
| Anticaking agent (anhydrous Magnesium sulphate) | 0.0200 |
| Dye(s) (Methyl Violet) | 0.0015 |
| Fillers (s) (Insilco and Kaolex) | 44.0331 |
| Total | 100.00% (w/w) |

The process for the preparation of the above composition comprises mixing thoroughly, for ½ hour, Imidacloprid, antimousse 426-R, Lisapol D, anhydrous Magnesium stearate, insilco, Kaolex, Acephate, magnesium stearate, Bitrex, Zeolite, and methyl violet in a pre-blender equipped with an agitator to get a homogenous mixture of all the ingredients. Thereafter, the homogenous mixture obtained is micronised to get a particle size of 2-10 microns which is post-blended to yield the synergistic insecticidal composition.

EXAMPLE-4

Process for the Preparation of a Synergistic Insecticidal Composition Containing Imidacloprid 2.5%+Acephate 55.0% [57.5% SP]:

Composition

| Ingredient | Quantity (% w/w) |
| --- | --- |
| Imidacloprid Techical (purity 95%) | 2.6316 |
| Acephate Technical (purity 97%) | 56.7011 |
| Stabilizer (Potassium alginate) | 4.0000 |
| Emetic agent (Amrex) | 0.0003 |
| Disintegrating agent (Zeolite) | 6.0000 |
| Antifoaming agent (Antimousse 426-R) | 0.1000 |
| Wetting cum dispersing agent (Lisapol-D) | 1.2500 |
| Anticaking agent (anhydrous Magnesium sulphate) | 0.0200 |
| Dye(s) (Ocean Blue) | 0.0020 |
| Fillers (s) (Insilco and kaolex) | 29.2950 |
| Total | 100.00% (w/w) |

The process of preparing the above composition comprises mixing thoroughly, for ½ hour, Imidacloprid, antimousse 426-R, Lisapol D, anhydrous Magnesium sulphate, insilco, Kaolex, Acephate, Potassium alginate, Amrex, Zeolite, and Ocean blue in the above said proportions in a pre-blender equipped with an agitator to get a homogenous mixture of all the ingredients. Thereafter, the homogenous mixture obtained is micronised to get a particle size of 2-10 microns which is post-blended to yield the synergistic insecticidal composition.

EXAMPLE-5

Process for the Preparation of a Synergistic Insecticidal Composition Containing Imidacloprid 1.8%+Acephate 50.0% [51.8% SP]:

Composition

| Ingredient | Quantity (% w/w) |
| --- | --- |
| Acephate active ingredient | 50.00 |
| Imidacloprid active ingredient | 1.80 |
| Surfactant—[Alkyl Naphthalene Sulfonate] | 3.00 |
| Inert carrier [Precipitated Silica] | 45.20 |
| Total | 100.00% w/w |

The process of preparing the above synergistic insecticidal composition comprises mixing thoroughly, for ½ hour, Acephate, Imidacloprid, Alkyl Naphthalene Sulfonate, and Precipitated Silica in the above mentioned proportions in a pre-blender equipped with an agitator to get a homogenous mixture of all the ingredients. Thereafter, the homogenous mixture obtained is micronised to get a particle size of 2-10 microns which is post-blended to yield the synergistic insecticidal composition.

EXAMPLE-6

Process for the Preparation of a Synergistic Insecticidal Composition Containing Imidacloprid 1.8%+Acephate 50% [51.8% Dry Flowable]:

Composition

| Ingredient | Quantity (% w/w) |
| --- | --- |
| Acephate Technical (purity 97%) | 51.5465 |
| Imidacloprid Techical (purity 95%) | 1.8948 |
| Stabilizer (Ammonium sulphate) | 3.0000 |
| Emetic agent (Bitrex) | 0.0002 |
| Disintegrating agent (Attapulgite) | 5.0000 |
| Antifoaming agent (Antimousse 426-R) | 0.1000 |
| Wetting cum dispersing agent (Lisapol-D) | 1.5000 |
| Anticaking agent (anhydrous Magnesium sulphate) | 0.0100 |
| Dye(s) (Ocean blue) | 0.0010 |
| Fillers (s) (Insilco and Kaolex) | 36.9475 |
| Total | 100.00% (w/w) |

The process of preparing the dry flowable synergistic insecticidal composition containing the above ingredients comprises mixing Acephate, Imidacloprid Techical (purity 95%), Ammonium sulphate, Bitrex, Attapulgite, Antimousse 426-R Lisapol-D, anhydrous Magnesium sulphate, ocean blue, Insilco and Kaolex in the above said proportions in a pre-blender equipped with an agitator to get a homogenous mixture of all the ingredients. Thereafter, the homogenous mixture obtained is micronised to get particle size of 2-10 microns which is post-blended to yield the synergistic insecticidal composition.

The resulting homogenous mixture is thereafter granulated through a granulator maintaining the inlet temperature in the range of 30-35° C. and the outlet temperature in the range of 40-45° C. and the rate and quantity of material fed to the granulator to minimize clumping together of the granulated product. The resulting product is conditioned, dried, sieved, sized and post-blended to yield the synergistic insecticidal composition in a dry flowable form.

EXAMPLE-7

Process for the Preparation of a Synergistic Insecticidal Composition Containing Imidacloprid 2.0%+Phosphamidon 40% [42% SP]:

Composition

| Ingredient | Quantity (% w/w) |
| --- | --- |
| Imidacloprid Technical (purity 95%) | 2.1053 |
| Phosphamidon Technical (purity 92%) | 43.4783 |
| Stabilizer (Priochem PN) | 2.0000 |
| Emetic agent (Bitrex) | 0.0030 |
| Disintegrating agent (Zeolite) | 5.0000 |
| Antifoaming agent (Antimousse 426-R) | 1.0000 |
| Wetting agent (Supragil MNS-90) | 3.0000 |
| Dispersing agent (Supragil WP) | 7.0000 |
| Binding agent (PVP K-30) | 0.5000 |
| Dye(s) (Methyl violet) | 0.5000 |
| Filler(s) (Insilco and Kaolex) | 35.4134 |
| Total | 100.00% (w/w) |

The process of preparing the above mentioned synergistic insecticidal composition, according to the present invention comprises mixing Imidacloprid Technical (purity 95%), Phosphamidon Technical (purity 92%), Priochem PN, Bitrex, Zeolite, Antimousse 426-R, Supragil MNS-90, Supragil WP, PVP K-30, Methyl violet, Insilco and Kaolex in the above said proportions in a pre-blender equipped with an agitator to get a homogenous mixture of all the ingredients. Thereafter, the homogenous mixture obtained is micronised to get particle size of 2-10 microns which is post-blended to yield the synergistic insecticidal composition.

EXAMPLE-8

Process for the preparation of a synergistic insecticidal composition containing Imidacloprid 3.0%+Phosphamidon 45.0% [48% SP]:

Composition

| Ingredient | Quantity (% w/w) |
| --- | --- |
| Imidacloprid Technical (purity 95%) | 3.1579 |
| Phosphamidon Technical (purity 92%) | 48.9131 |
| Stabilizer (Priochem BL) | 2.5000 |
| Emetic agent (Amerex) | 0.0040 |
| Disintegrating agent (Zeolite) | 6.0000 |
| Antifoaming agent (Antimousse 426-R) | 0.7500 |
| Wetting agent (Supragil MNS-90) | 2.0000 |
| Dispersing agent (Supragil WP) | 7.0000 |
| Binding agent (Agrimer) | 0.2000 |
| Dye(s) (Ocean blue) | 0.6000 |
| Filler(s) (Insilco and kaolex) | 28.8750 |
| Total | 100.00% (w/w) |

The process of preparing the above mentioned synergistic insecticidal composition comprises mixing Imidacloprid Technical (purity 95%), Phosphamidon Technical (purity 92%), priochem BL, Amerex, Zeolite, Antimousse 426-R, Supragil MNS-90, Supragil WP, Agrimer, Ocean blue, Insilco and kaolex in the above said proportions in a pre-blender equipped with an agitator to get a homogenous mixture of all the ingredients. Thereafter, the homogenous mixture obtained is micronised to get a particle size of 2-10 microns which is post-blended to yield the synergistic insecticidal composition.

EXAMPLE-9

Process for the Preparation of a Synergistic Insecticidal Composition Containing Imidacloprid 1.0%+Phosphamidon 40.0% [41% SP]:

Composition

| Ingredient | Quantity (% w/w) |
| --- | --- |
| Imidacloprid Technical (purity 95%) | 1.0527 |
| Phosphamidon Technical (purity 92%) | 43.4783 |
| Stabilizer (Priochem PN) | 3.0000 |
| Emetic agent (Bitrex) | 0.0030 |
| Disintegrating agent (Zeolite) | 7.0000 |
| Antifoaming agent (Antimousse 426-R) | 1.0000 |
| Wetting agent (Supragil WP) | 4.0000 |
| Dispersing agent (Supragil MNS-90) | 7.5000 |
| Binding agent (VA-6) | 0.4000 |
| Dye(s) (Methyl violet) | 0.4000 |
| Filler(s) (Insilco and Kaolex) | 32.1660 |
| Total | 100.00% (w/w) |

The above synergistic insecticidal composition is prepared by thoroughly mixing Imidacloprid Technical (purity 95%), Phosphamidon Technical (purity 92%), Priochem PN, Bitrex, Zeolite, Antimousse 426-R, Supragil WP, Supragil MNS-90, VA-6, Methyl violet, Insilco and Kaolex in the above said proportions in a pre-blender equipped with an agitator to get a homogenous mixture of all the ingredients. Thereafter, the homogenous mixture obtained is micronised to get a particle size of 2-10 microns which is post-blended to yield the synergistic insecticidal composition.

EXAMPLE-10

Process for the preparation of a synergistic insecticidal composition containing Imidacloprid 2.0%+Phosphamidon 40% [42% SP]:

Composition

| Ingredient | Quantity (% w/w) |
| --- | --- |
| Phosphamidon active ingredient | 40.0000 |
| Imidacloprid active ingredient | 2.0000 |
| Surfactant—(Alkyl Naphthalene Sulfonate) | 7.0000 |
| Dye(s)—(Methyl violet) | 0.0500 |
| Fillers—Inert (Precipitated Silica) | 50.9500 |
| Total | 100.00% (w/w) |

The process for the preparation of the synergistic insecticidal composition according to the present invention comprises mixing Phosphamidon active ingredient, Imidacloprid active ingredient, Alkyl Naphthalene Sulfonate, Methyl violet and Precipitated Silica in the above said proportions in a pre-blender equipped with an agitator to get a homogenous mixture of all the ingredients. Thereafter, the homogenous mixture obtained is micronised to get particle size of 2-10 microns which is post-blended to yield the synergistic insecticidal composition.

EXAMPLE-11

Evaluation of the synergistic insecticidal effect of the Chloronicotynyle compound (Imidacloprid) plus a second insecticide Organophosphorus compound (Acephate, Phosphamidon) can be established by using any synergistic insecticidal composition prepared by the process described in the above examples. For these evaluations one or more of the synergistic insecticidal compositions prepared in the examples are used here.

In this evaluation, Brown plant hoppers and Green plant hoppers are obtained from laboratory colonies. Paddy leaves are immersed in 1:1 v/v, acetone/water solutions of the test compound, or solution of a combination of the test compounds, for a period of about 4 seconds. Following immersion, leaves are allowed to air-dry for 2-3 hours. Plastic bioassay trays containing multiple open-faced wells (4.0×4.0× 2.5 cm) are used. Cut portions of a treated leaf, a moistened cotton dental wick and a single third-instar larva are placed into each well. These wells are covered with an adhesive vented clear plastic sheet which is held under constant fluorescent light at about 30° C. for a predetermined period of time. Larval mortality/morbidity is evaluated at 5 days after treatment. All treatments are replicated 3-4 fold in a randomized complete block design with 15-30 larvae per treatment. Using conventional log-probit analysis, the $LC_{50}$ of each treatment is determined.

Using the above process, a Chloronicotynyle compound may be evaluated alone and in combination with a second insecticidal compound, Imidacloprid, at dose rates of 0, 15, 18, 21, 24, 27 and 30 ppm and in combination with Acephate 0, 400, 500, 600, 700, 800 ppm in various combination of these strengths.

The other insecticidal compound, Phosphamidon, by using the above process, may be evaluated alone and in combination with a second insecticidal compound, Imidacloprid at dose rates of 0, 11, 14, 17, 20, 27 and 30 ppm and in combination with Phosphamidon 0, 160, 200, 240, 280, 320, 370, 400 ppm in various combination of these strengths. Treatments which are used are shown in Table 1.

TABLE 1

| Second active compound | Dose Rate (ppm) | Imidacloprid Dose Rate (ppm) | | | | | | |
|---|---|---|---|---|---|---|---|---|
| Acephate | 0 | 0 | 15 | 18 | 21 | 24 | 27 | 30 |
|  | 400 | 0 | 15 | 18 | 21 | 24 | 27 | 30 |
|  | 500 | 0 | 15 | 18 | 21 | 24 | 27 | 30 |
|  | 600 | 0 | 15 | 18 | 21 | 24 | 27 | 30 |
|  | 700 | 0 | 15 | 18 | 21 | 24 | 27 | 30 |
|  | 800 | 0 | 15 | 18 | 21 | 24 | 27 | 30 |
| Phosphamidon | 0 | 0 | 11 | 14 | 17 | 20 | 27 | 30 |
|  | 160 | 0 | 11 | 14 | 17 | 20 | 27 | 30 |
|  | 200 | 0 | 11 | 14 | 17 | 20 | 27 | 30 |
|  | 240 | 0 | 11 | 14 | 17 | 20 | 27 | 30 |
|  | 280 | 0 | 11 | 14 | 17 | 20 | 27 | 30 |
|  | 320 | 0 | 11 | 14 | 17 | 20 | 27 | 30 |
|  | 370 | 0 | 11 | 14 | 17 | 20 | 27 | 30 |
|  | 400 | 0 | 11 | 14 | 17 | 20 | 27 | 30 |

The results of the above experiment shows that out of a large number of the above all combinations tried, some of them shows the synergistic insecticidal control. These combinations are shown in the bold values in the above table.

The following example confirm the synergistic effect of the strength selected from the Eample-11.

EXAMPLE-12

Synergism can be calculated by using the Colby's method i.e. the expected (or predicted) response of the combination is calculated by taking the product of the observed response for each individual component of the combination when applied alone divided by 100 and subtracting this value from the sum of observed response for each component when applied alone. Synergism of the combination is then determined by comparing the observed response of the combination to the expected (or predicted) response as calculated from the observed response of each individual component alone. If the observed response of the combination is greater than the expected (or predicted) response then the combination is said to be synergistic and falls within the definition of synergistic effect. (Colby, S. R., Weeds, 1967(15), p. 20-22).

TABLE 2

Synergistic insecticidal effect of a combination of Imidacloprid + Acephate

| S. No. | Imidacloprid (ppm) | Acephate (ppm) | Observed Mortality % | Expected Mortality % | Difference |
|---|---|---|---|---|---|
| 1 | 24 | 0 | 55.00 | — | — |
| 2 | 27 | 0 | 69.25 | — | — |
| 3 | 30 | 0 | 72.10 | — | — |
| 4 | 0 | 600 | 52.50 | — | — |
| 5 | 0 | 700 | 60.00 | — | — |
| 6 | 0 | 800 | 70.00 | — | — |
| 7 | 24 | 600 | 70.00 | 78.63 | −8.63 |
| 8 | 24 | 700 | 71.75 | 82.00 | −10.25 |
| 9 | 24 | 800 | 93.00 | 86.50 | 6.50 |
| 10 | 27 | 600 | 88.8 | 85.40 | 2.60 |
| 11 | 27 | 700 | 91.00 | 87.70 | 3.30 |
| 12 | 27 | 800 | 97.05 | 90.78 | 6.27 |
| 13 | 30 | 600 | 90.00 | 86.75 | 3.25 |
| 14 | 30 | 700 | 95.00 | 88.84 | 6.16 |
| 15 | 30 | 800 | 99.5 | 91.63 | 7.87 |

As can be seen from the data shown in Table 2, combinations of Imidacloprid plus a organophosphorus compound (Acephate) demonstrate synergistic insect control.

TABLE 3

Synergistic insecticidal effect of a combination of Imidacloprid + Phosphamidon

| S. No. | Imidacloprid (ppm) | Phosphamidon (ppm) | Observed Mortality % | Expected Mortality % | Difference |
|---|---|---|---|---|---|
| 1 | 20 | 0 | 47.30 | — | — |
| 2 | 27 | 0 | 69.25 | — | — |
| 3 | 30 | 0 | 72.1 | — | — |
| 4 | 0 | 320 | 60.0 | — | — |
| 5 | 0 | 370 | 65 | — | — |
| 6 | 0 | 400 | 72.0 | — | — |
| 7 | 20 | 320 | 83.03 | 78.92 | 4.11 |
| 8 | 20 | 370 | 88.91 | 81.56 | 7.41 |
| 9 | 20 | 400 | 91.04 | 85.24 | 5.80 |
| 10 | 27 | 320 | 89.00 | 87.70 | 1.30 |
| 11 | 27 | 370 | 92.03 | 89.24 | 2.79 |
| 12 | 27 | 400 | 94.00 | 91.39 | 2.61 |
| 13 | 30 | 320 | 93.00 | 88.84 | 4.16 |

TABLE 3-continued

Synergistic insecticidal effect of a combination of
Imidacloprid + Phosphamidon

| S. No. | Imidacloprid (ppm) | Phosphamidon (ppm) | Observed Mortality % | Expected Mortality % | Difference |
|---|---|---|---|---|---|
| 14 | 30 | 370 | 95.00 | 90.24 | 4.76 |
| 15 | 30 | 400 | 98.00 | 92.19 | 5.81 |

As can be seen from the data shown in Table 3, combinations of Imidacloprid plus a organophosphorus compound (Phosphamidon) demonstrate synergistic insect control.

EXAMPLE 13

The following provides the evaluation of the synergistic insecticidal effect of a combination of Chloronicotynyle compounds (Imidacloprid) plus Organophosphorus compounds (Acephate) against pests of Paddy.

In this example most of the synergistic insecticidal compositions prepared by the process described in this invention are used to evaluate their activities.

In this evaluation, percent mortality of hoppers is worked out based on the number of hoppers counted before and after sprays and based on dead heart counts before and after sprays. The data is averaged and analyzed for the test of significance.

Details of the Experiment:
a. Design: Randomised block design
b. Replication: Three
c. Product: Imidacloprid+Acephate (1.8+50) %
d. Treatment: Seven (as shown in details in the Table-4)

TABLE 4

(Details of the treatments done)

| S. No. | Active Ingredient (g a.i./ha) dose | Formulation quantity (g/ha) |
|---|---|---|
| 1 | Imidacloprid + Acephate 311 | 600 |
| 2 | Imidacloprid + Acephate 388.8 | 750 |
| 3 | Imidacloprid + Acephate 518 | 1000 |
| 4 | Imidacloprid + Acephate 647.5 | 1250 |
| 5 | Imidacloprid 17.8% SL 20 | 112 |
| 6 | Acephate 75% SP 585 | 780 |
| 7 | Water spray only | |

Imidacloprid + Acephate (1.8 + 50) % at 2000 and 4000 g/ha laid out separately by the side of bio-efficacy trial plot to avoid drift of chemical.

e. Plot size: 5×4 m=20 sq. m.
f. Variety: Jyothi
g. Spacing: 20×10 cm
h. Fertilizer: 100:50:50 NPK Kg/ha
i. Sprayer used: Knapsack sprayer
j. Spray volume: 1.5 litre per 20 sq. m. plot
k. Time of application: When the hoppers and dead heart symptom are noticed.
l. Method: Required quantity of spray fluid is prepared before spray application and for phytotoxicity studies concentration of Imidacloprid+Acephate (1.8+50) % at 2000 and 4000 g/ha is laid out separately by the side of the bio-efficacy trial plot to avoid drift of the chemical.
m. Observations recorded: i. Pre and post treatment data of green leaf hopper in three leaves from the base, middle and top position of the plants, brown plant hoppers on the stem portions.
  ii. Phytotoxicity of higher concentrations.
  iii. Grain yield.
n. Method of Observation: Phytotoxicity in terms of yellowing or blightening of leaves is recorded in the higher concentrations of 2000 and 4000 g/ha. When the crop attained maturity the ear heads are harvested, dried, threshed and grain yield per 20 sq. m. plot is recorded and it is then computed to quintals per hectare. The data is analyzed statistically to discriminate the treatment superiority for control leaf eating pests and variation in the yield.
o. Results: The results of the field trial carried out to evaluate the bioefficacy of and standardization of doses of Imidacloprid+Acephate (1.8+50) % at doses 600, 750, 1000, 1250 g/ha as compared Imidacloprid 17.8% SL 20 g/ha, Acephate 75% SP 780 g/ha and untreated check are presented in the following tables.

TABLE 5

Mortality (%) Brown plant hoppers on days after Imidacloprid + Acephate
(1.8 + 50) % spray application

| S. No. | Treatment in g a.i./ha | Dose g/ha | Pre-count | Mortality 10 DAT after 1 spray | Pre-count | Mortality 10 DAT after 2nd spray | Mean mortality due to two sprays |
|---|---|---|---|---|---|---|---|
| 1 | Imidacloprid + Acephate (1.8 + 50) % 311 | 600 | 15 | 70.5 | 11 | 65 | 67.75 |
| 2 | Imidacloprid + Acephate (1.8 + 50) % 388.5 | 750 | 11.1 | 71 | 10.5 | 70 | 70.5 |
| 3 | Imidacloprid + Acephate (1.8 + 50) % 518 | 1000 | 14.1 | 71.5 | 10.4 | 72 | 71.75 |
| 4 | Imidacloprid + Acephate (1.8 + 50) % 647.5 | 1250 | 12.1 | 72 | 9.5 | 72.1 | 72.05 |
| 5 | Imidacloprid 17.8 SL @ 20 g a.i./ha | 112 | 17 | 69.5 | 11 | 69 | 69.25 |

TABLE 5-continued

Mortality (%) Brown plant hoppers on days after Imidacloprid + Acephate (1.8 + 50) % spray application

| S. No. | Treatment in g a.i./ha | Dose g/ha | Pre-count | Mortality 10 DAT after 1 spray | Pre-count | Mortality 10 DAT after 2nd spray | Mean mortality due to two sprays |
|---|---|---|---|---|---|---|---|
| 6 | Acephate 75% SP @ 585 g a.i./ha | 780 | 15.16 | 69 | 10 | 71 | 70 |
| 7 | Water spray | — | 16.2 | −20 | 20 | −35 | −27.5 |

TABLE 6

Mortality (%) of green plant hoppers on days after spray application

| S. No. | Treatment in g a.i./ha | Dose g/ha | Pre-count | Mortality 10 DAT after 1 spray | Pre-count | Mortality 10 DAT after 2nd spray | Mean mortality due to two sprays |
|---|---|---|---|---|---|---|---|
| 1 | Imidacloprid + Acephate (1.8 + 50) % 311 | 600 | 7.11 | 64 | 6.12 | 63 | 63.5 |
| 2 | Imidacloprid + Acephate (1.8 + 50) % 388.5 | 750 | 8.61 | 65.1 | 7.12 | 62.3 | 63.7 |
| 3 | Imidacloprid + Acephate (1.8 + 50) % 518 | 1000 | 8.6 | 68.1 | 8 | 63.1 | 65.6 |
| 4 | Imidacloprid + Acephate (1.8 + 50) % 647.5 | 1250 | 10.1 | 74.1 | 8.7 | 68.7 | 71.4 |
| 5 | Imidacloprid 17.8 SL @ 20 g a.i./ha | 112 | 9.11 | 68.1 | 7.15 | 66.66 | 67.38 |
| 6 | Acephate 75% SP @ 585 g a.i./ha | 780 | 7.7 | 67.5 | 8 | 67.15 | 67.32 |
| 7 | Water spray | — | 8.1 | −6.6 | 7.8 | −12.5 | −9.55 |

Conclusion

From Table-5 and 6, Imidacloprid+Acephate (1.8+50) % at concentrations of 1000 and 1250 g/ha are effective and superior at first and second sprays respectively which are superior and or on par with standard checks tested against green leaf hoppers Imidacloprid+Acephate (1.8+50) % at 1250 is highly effective while @1000 g is as effective as standard checks after the first spray. After a second spray at 1000 and 1250 g are on par with standard checks.

TABLE 7

Reduction (%) of dead hearts due to stem borer after pesticide application

| S. No. | Treatment in g a.i./ha | Dose g/ha | Pre-count | Reduction after 1 spray | Reduction after 2nd spray | Mean reduction of two sprays |
|---|---|---|---|---|---|---|
| 1 | Imidacloprid + Acephate (1.8 + 50) % 311 | 600 | 6.5 | 58 | 60 | 59 |
| 2 | Imidacloprid + Acephate (1.8 + 50) % 388.5 | 750 | 8.91 | 61.12 | 65.6 | 63.36 |
| 3 | Imidacloprid + Acephate (1.8 + 50) % 518 | 1000 | 9.91 | 65.35 | 70.1 | 67.72 |
| 4 | Imidacloprid + Acephate (1.8 + 50) % 647.5 | 1250 | 10.15 | 70.15 | 72.1 | 71.13 |
| 5 | Imidacloprid 17.8 SL @ 20 g a.i./ha | 112 | 9.15 | 68.18 | 69.5 | 68.84 |

TABLE 7-continued

Reduction (%) of dead hearts due to stem borer after pesticide application

| S. No. | Treatment in g a.i./ha | Dose g/ha | Pre-count | Reduction after 1 spray | Reduction after 2nd spray | Mean reduction of two sprays |
|---|---|---|---|---|---|---|
| 6 | Acephate 75% SP @ 585 g a.i./ha | 780 | 8.15 | 66.15 | 67.1 | 66.63 |
| 7 | Water spray | — | 8.9 | −2.9 | −8.1 | −5.5 |

Conclusion

From Table-7 against stem borers Imidacloprid+Acephate (1.8+50) % at 1250 is on par with Imidacloprid and at 1000 is on par with Acephate and differed from other treatments. Imidacloprid+Acephate (1.8+50) % at 1250 g/ha proved superior followed by 1000 g/ha which is on par with Imidacloprid. Imidacloprid+Acephate (1.8+50) % at 750 g/ha is on par with Acephate at 780 g/ha after second spray.

TABLE 8

Grain yield after spray application

| S. No. | Treatment in g a.i./ha | Dose g/ha | Grian yield (Quintal/ha) |
|---|---|---|---|
| 1 | Imidacloprid + Acephate (1.8 + 50) % 311 | 600 | 134.65 |
| 2 | Imidacloprid + Acephate (1.8 + 50) % 388.5 | 750 | 138.5 |
| 3 | Imidacloprid + Acephate (1.8 + 50) % 518 | 1000 | 138.6 |
| 4 | Imidacloprid + Acephate (1.8 + 50) % 647.5 | 1250 | 138.8 |
| 5 | Imidacloprid 17.8 SL @ 20 g a.i./ha | 112 | 136.5 |
| 6 | Acephate 75% SP @ 585 g a.i./ha | 780 | 92 |
| 7 | Water spray | — | 77.5 |

Conclusion

Grain yield levels, as shown in Table-8, are maximum in Imidacloprid+Acephate (1.8+50) % at all concentrations which is on par with Imidacloprid @ 112 ml/ha and differed significantly from Acephate @ 780 g/ha. Phytoxocity levels at 2000 and 4000 g/ha varied from 2-3% leaf injury.

TABLE 9

Phytotoxicity due to application of pesticides

| S. No. | Treatment in g a.i./ha | Dose g/ha | * Cumulative Phytotoxicity (%) on 14 th day |
|---|---|---|---|
| 1 | Imidacloprid + Acephate (1.8 + 50) % 311 | 600 | NP |
| 2 | Imidacloprid + Acephate (1.8 + 50) % 388.5 | 750 | NP |
| 3 | Imidacloprid + Acephate (1.8 + 50) % 518 | 1000 | NP |
| 4 | Imidacloprid + Acephate (1.8 + 50) % 647.5 | 1250 | NP |
| 5 | Imidacloprid + Acephate (1.8 + 50) % 1036 | 2000 | 2.00% |
| 6 | Imidacloprid + Acephate (1.8 + 50) % 2072 | 4000 | 3.00% |
| 7 | Imidacloprid 17.8 SL @ 20 g a.i./ha | 112 | NP |
| 8 | Acephate 75% SP @ 585 g a.i./ha | 780 | NP |
|  | Water spray | — | NP |

NP = No phytoxocity
* = Observation for phytoxicity was taken for 14 days after sprayon necrosis, hyponasty, leaf tip injury, leaf surface injury, wilting, vein clearing etc.

Conclusion

Imidacloprid+Acephate (1.8+50) % at 1000 and 1250 g/ha are effective against BPH, GLH and stem borers. Irrespective of concentrations grain yields are superior over standard checks. Phytotoxicity is negligible (2 and 3%) at the highest concentrations of 2000 and 4000 g/ha.

EXAMPLE-14

The following provides an evaluation of the synergistic insecticidal effect of a combination of Chloronicotynyle compounds (Imidacloprid) plus Organophosphorus compounds (Phosphamidon) against pests of Paddy.

In this example most of the synergistic insecticidal composition prepared by the process described in this invention is used to evaluate their activities.

In this evaluation, percent mortality of hoppers is worked out based on the number of hoppers counted before and after sprays and based on dead heart counts before and after sprays. The data is averaged and analyzed for the test of significance.

Details of the Experiment:
a. Design: Randomised block design
b. Replication: Three
c. Product: Imidacloprid+Phosphamidon (2+40) %
d. Treatment: Eight (Table-10 describes the eight treatments, in details, studied during this example).

TABLE 10

(Details of the treatments studied)

| S. No. | Active Ingredient (g a.i./ha) dose | Formulation quantity (g/ha) |
|---|---|---|
| 1 | Imidacloprid + Phosphamidon 126 | 300 |
| 2 | Imidacloprid + Phosphamidon 168 | 400 |
| 3 | Imidacloprid + Phosphamidon 210 | 500 |
| 4 | Imidacloprid + Phosphamidon 252 | 600 |
| 5 | Imidacloprid + Phosphamidon 294 | 700 |
| 6 | Imidacloprid 17.8% SL 20 | 112 |
| 7 | Phosphamidon 40% SL 300 | 750 |
| 8 | Water spray only | |

Imidacloprid + Phosphamidon (2 + 40) % at 1200 and 2400 g/ha laid out separately by the side of bio-efficacy trial plot to avoid drift of chemical.

e. Plotsize: 5×4 m=20 sq.m.
f. Variety: Jyothi
g. Spacing: 20×10 cm
h. Fertilizer: 100:50:50 NPK Kg/ha
i. Sprayer used: Knapsack sprayer
j. Spray volume: 1.5 litre per 20 sq. m. plot
k. Time of application: When the hoppers and dead heart symptom are noticed.
l. Method: Required quantity of spray fluid is prepared before spray application and for phytotoxicity studies concentration of Imidacloprid+Phosphamidon (2+40) % at 1200 and 2400 g/ha is laid out separately by the side of the bio-efficacy trial plot to avoid drift of the chemical.

m. Observations recorded: i. Pre and post treatment data of green leaf hopper in three leaves from the base, middle and top position of he plants, brown plant hoppers on the stem portions.

o. Results: The results of the field trial carried out to evaluate the bioefficacy of and standardisation of doses of Imidacloprid+Phosphamidon (2+40) % at doses 300, 400, 500, 600 and 700 g/ha as compared Imidacloprid 17.8% SL 20 g/ha, Phosphamidon 40% SL 300 g/ha and untreated check are presented in the following tables.

TABLE 11

Mortality (%) Brown plant hoppers on days after Imidacloprid + Phosphamidon (2 + 40) % spray application

| S. No. | Treatment g a.i./ha | Dose g/ha | Pre-count | Mortality 10 DAT after 1 spray | Pre-count | Mortality 10 DAT after $2^{nd}$ spray | Mean mortality due to two sprays |
|---|---|---|---|---|---|---|---|
| 1 | Imidacloprid + Phosphamidon 126 | 300 | 18.66 | 72.1 | 10.2 | 69.34 | 70.72 |
| 2 | Imidacloprid + Phosphamidon 168 | 400 | 12.88 | 73.16 | 10.63 | 71.33 | 72.24 |
| 3 | Imidacloprid + Phosphamidon 210 | 500 | 16.1 | 71.66 | 10.83 | 77 | 74.33 |
| 4 | Imidacloprid + Phosphamidon 252 | 600 | 12.1 | 78.66 | 8.93 | 82 | 80.33 |
| 5 | Imidacloprid + Phosphamidon 294 | 700 | 17.2 | 88.95 | 10.93 | 87 | 87.97 |
| 6 | Imidacloprid 17.8% SL 20 | 112 | 17.14 | 69.66 | 10.56 | 70 | 69.83 |
| 7 | Phosphamidon 40% SL 300 | 750 | 18.66 | 71.66 | 12.33 | 72.33 | 71.99 |
| 8 | Water spray only | | 19.21 | −28.69 | 19.38 | −37.66 | −33.18 |

TABLE 12

Mortality (%) of green plant hoppers on days after spray application

| S. No. | Treatment g a.i./ha | Dose g/ha | Pre-count | Mortality 10 DAT after 1 spray | Pre-count | Mortality 10 DAT after $2^{nd}$ spray | Mean mortality due to two sprays |
|---|---|---|---|---|---|---|---|
| 1 | Imidacloprid + Phosphamidon 126 | 300 | 8.73 | 67 | 7.33 | 65 | 66 |
| 2 | Imidacloprid + Phosphamidon 168 | 400 | 9.33 | 69.33 | 8 | 63.33 | 66.33 |
| 3 | Imidacloprid + Phosphamidon 210 | 500 | 10.16 | 71 | 8.3 | 65.66 | 68.33 |
| 4 | Imidacloprid + Phosphamidon 252 | 600 | 7.5 | 80.66 | 9.83 | 73.33 | 76.99 |
| 5 | Imidacloprid + Phosphamidon 294 | 700 | 10.33 | 85.33 | 7.6 | 80.66 | 82.99 |
| 6 | Imidacloprid 17.8% SL 20 | 112 | 7.75 | 68 | 9.33 | 70.66 | 69.33 |
| 7 | Phosphamidon 40% SL 300 | 750 | 9.33 | 67.66 | 9.75 | 71.33 | 69.5 |
| 8 | Water spray only | | 8.16 | −20 | 8.5 | −18 | −19 | ii. Phytotoxicity of higher concentrations.
iii. Grain yield.

n. Method of Observation: Phytotoxicity in terms of yellowing or blightening of leaves is recorded in the higher concentrations of 1200 and 2400 g/ha.

When the crop-attained maturity the ear heads are harvested, dried, threshed and grain yield per 20 sq. m. plot is recorded and it is then computed to quintals per hectare. The data is analyzed statistically to discriminate the treatment superiority for control leaf eating pests and variation in the yield.

Conclusion

From Tables 11 and 12, toxicity of Imidacloprid+Phosphamidon (2+40) % increased with increase in the concentrations. Against brown plant hoppers Imidacloprid+Phosphamidon (700 g) is superior followed by its doses at 500 and 600 gm which differed significantly over other insecticides tested. Trend is similar after second spray. Maximum mortality of green leaf hoppers is at 700 g/ha and the toxicity differed significantly over other toxicants. Similar trend remained even after second spray.

TABLE 13

Reduction (%) of dead hearts disease due to stem borer after pesticide application

| S. No. | Treatment in g a.i./ha | Dose g/ha | Pre-count | Reduction after 1 spray | Reduction after 2nd spray | Mean reduction of two sprays |
|---|---|---|---|---|---|---|
| 1 | Imidacloprid + Phosphamidon 126 | 300 | 7.23 | 56.12 | 59.92 | 58.02 |
| 2 | Imidacloprid + Phosphamidon 168 | 400 | 12.81 | 61.82 | 72.65 | 67.23 |
| 3 | Imidacloprid + Phosphamidon 210 | 500 | 9.98 | 67.35 | 80.98 | 74.17 |
| 4 | Imidacloprid + Phosphamidon 252 | 600 | 15.13 | 70.08 | 81.6 | 75.84 |
| 5 | Imidacloprid + Phosphamidon 294 | 700 | 6.62 | 70.16 | 82.7 | 76.43 |
| 6 | Imidacloprid 17.8% SL 20 | 112 | 7.17 | 72.15 | 78.19 | 75.17 |
| 7 | Phosphamidon 40% SL 300 | 750 | 7.75 | 66.13 | 70.83 | 68.48 |
| 8 | Water spray only | | 11.02 | 20.01 | 15.65 | 17.83 |

Conclusion

From Table 13, against stem borers, the maximum reduction of dead hearts is noticed in the Imidacloprid+Phosphamidon (2+40) % at 600 and 700 g/ha which differed from other toxicants. But, it is inferior to Imidacloprid. However, after second spray Imidacloprid+Phosphamidon (2+40) at 500 to 700 g are superior over other pesticides tested.

TABLE 14

Grain yield after spray application

| S. No. | Treatment in g a.i./ha | Dose g/ha | Grian yield (Quintal/ha) |
|---|---|---|---|
| 1 | Imidacloprid + Phosphamidon 126 | 300 | 87.65 |
| 2 | Imidacloprid + Phosphamidon 168 | 400 | 101.65 |
| 3 | Imidacloprid + Phosphamidon 210 | 500 | 105.15 |
| 4 | Imidacloprid + Phosphamidon 252 | 600 | 118.15 |
| 5 | Imidacloprid + Phosphamidon 294 | 700 | 119.65 |
| 6 | Imidacloprid 17.8% SL 20 | 112 | 92 |
| 7 | Phosphamidon 40% SL 300 | 750 | 111.18 |
| 8 | Water spray only | | 77.5 |

Conclusion

From Table 14, the grain yield levels are maximum in Imidacloprid+Phosphamidon (2+40) % up to 700 g/ha which is on par with 600 g/ha and it differed significantly over 500, 400 and 300 g/ha and others chemicals tested.

TABLE 15

Phytotoxicity due to application of pesticides

| S. No. | Treatment in g a.i./ha | Dose g/ha | * Cumulative Phytotoxicity (%) on 14 th day |
|---|---|---|---|
| 1 | Imidacloprid + Phosphamidon 126 | 300 | NP |
| 2 | Imidacloprid + Phosphamidon 168 | 400 | NP |
| 3 | Imidacloprid + Phosphamidon 210 | 500 | NP |
| 4 | Imidacloprid + Phosphamidon 252 | 600 | NP |
| 5 | Imidacloprid + Phosphamidon 294 | 700 | NP |
| 6 | Imidacloprid + Phosphamidon 504 | 1200 | 1.00% |
| 7 | Imidacloprid + Phosphamidon 1008 | 2400 | 2.00% |
| 8 | Imidacloprid 17.8% SL 20 | 112 | NP |
| 9 | Phosphamidon 40% SL 300 | 750 | NP |
| 10 | Water spray only | | NP |

NP = No phytoxocity
* = Observation for phytoxicity was taken for 14 days after sprayon necrosis, hyponasty, leaf tip injury, leaf surface injury, wilting, vein clearing etc.

Conclusion

From Table 15, the phytoxocity is negligible in Imidacloprid+Phosphamidon (2+40) % at 300 to 700 g/ha and are at 1-2% in highest concentrations of 1200 and 2400 g/ha.

Results

Imidacloprid+Phosphamidon (2+40) % at 300 and 700 g/ha reduced hoppers and stem borers effectively. However, doses at 700 g is most effective followed by 400 and 500 g and on par with standard check chemicals even at 300 g/ha. The yields increased with the concentrations of Imidacloprid+Phosphamidon (2+40)% up to 700 g/ha. Phytotoxicity is negligible at all concentrations of Imidacloprid+Phosphamidon (2+40)% and even at 1200 to 2400 g/ha which recorded 1-2% leaf brightening.

The synergistic insecticidal composition prepared by the process of this invention can be applied as per prescribed recommendation on the label by mixing the pesticide and water at right dosage and spray. It can be sprayed by using high volume sprayer viz. Knapsack sprayer, using 500-1000 litres of water per hactare.

Although the present invention has been disclosed in terms of a preferred embodiment, it will be understood that numerous additional modifications and variations could be made thereto without departing from the scope of the invention as defined by the following claims:

We claim:

1. A synergistic insecticidal composition comprising
   a) 0.1 to 5% by weight of a Chloronicotynyle compound of Imidacloprid,
   b) 30 to 75% by weight of an Organophosphorus compound of Acephate, said Chloronicotynyle compound and said Organophosphorus compound are the only insecticidally active ingredients, and
   c) 20 to 69.9% by weight of at least one agriculturally acceptable compound selected from the group consisting of a conventional agriculturally acceptable carrier and a conventional agriculturally acceptable excipient.

2. The synergistic insecticidal composition of claim 1 wherein said at least one agriculturally acceptable compound is selected from the group consisting of silicas, silica gels, silicates, talc, kaolin, montmorillonite, attapulgite, pumice, sepiolite, bentonite, limestone, lime, chalk, clay, dolomite, diatomaceous earth, calcite, calcium sulfate, magnesium sulfate, magnesium sulfate, magnesium oxide, sand, ammonium sulfate, ammonium phosphate, ammonium nitrate, ureas, cereal meal, tree bark meal, wood meal, nutshell meal, and cellulose powders.

3. The synergistic insecticidal composition of claim 1 further comprising a surfactant selected from the group consisting of non-ionic surfactants, cationic surfactants and anionic surfactants.

4. The synergistic insecticidal composition of claim 3 wherein the anionic surfactants are selected from a group consisting of alkali metal soaps, alkaline earth metal soaps, substituted or unsubstituted ammonium salts of higher fatty acids, the sodium or potassium salt of oleic or stearic acid, and natural fatty acid mixtures.

5. The synergistic insecticidal composition of claim 1 further comprising a stabilizer.

6. The synergistic insecticidal composition of claim 5 wherein said stabilizer is selected from the group consisting of ethoxylates of vegetable oil, salts of higher fatty acids, a blend of the derivatives of epoxylated vegetable oil, Ethoxylated polyoxyethylene amine and pyrrolidine, and lactone.

7. The synergistic insecticidal composition of claim 1 further comprising a wetting cum dispersing agent.

8. The synergistic insecticidal composition of claim 7 wherein said wetting cum dispersing agent is selected from the group consisting of alkyl phenol ethoxylate, salts of alkyl naphthyl sulphonate, salts of alkyl aryl sulphonate, and derivative of sulfonated fatty alcohol.

9. The synergistic insecticidal composition of claim 1 further comprising a wetting agent.

10. The synergistic insecticidal composition of claim 9 wherein said wetting agent is a calcium or sodium salt of alkyl aryl sulphonate.

11. The synergistic insecticidal composition of claim 1 further comprising an emetic agent.

12. The synergistic insecticidal composition of claim 11 wherein said emetic agent is a lignocaine derivative or a formulation of lignocaine derivative.

13. The synergistic insecticidal composition of claim 1 further comprising an antifoaming agent.

14. The synergistic insecticidal composition of claim 13 wherein the antifoaming agent is a silicone oil derivative.

15. The synergistic insecticidal composition of claim 1 further comprising a disintegrating agent.

16. The synergistic insecticidal composition of claim 15 wherein the disintegrating agent is selected from a group consisting of bentonite clay, Zeolite clay, Attapulgite clay, sodium sulphate slats, and aluminum sulphate salts.

17. The synergistic insecticidal composition of claim 1 further comprising a filler.

18. The synergistic insecticidal composition of claim 17 wherein the filler is selected from a group consisting of silica, kaoline, and clay.

19. The synergistic insecticidal composition of claim 1 wherein said agriculturally acceptable compound includes said carrier and said excipient present in a ratio of carrier: excipient in a ratio of 1:1 to 1:10000.

20. The synergistic insecticidal composition of claim 1 further comprising an anticaking agent.

21. The synergistic insecticidal composition of claim 20 wherein the anticaking agent is selected from the group consisting of fumed silica, anhydrous Magnesium sulphate, a blend of sucrose and starch derivatives.

22. The synergistic insecticidal composition of claim 1 further comprising a dye.

23. The synergistic insecticidal composition of claim 22 wherein said dye is a water soluble dye of a water insoluble dye.

24. The synergistic insecticidal composition of claim 1 wherein said Acephate is Technical grade Acephate having a minimum of 97% purity.

25. The synergistic insecticidal composition of claim 1 wherein said Imidacloprid is Technical grade Imidacloprid having a minimum of 95% purity.

26. The synergistic insecticidal composition of claim 1 further comprising a dispersing agent.

27. The synergistic insecticidal composition of claim 26 wherein said dispersing agent is formaldehyde condensate of alkyl phenols.

28. The synergistic insecticidal composition of claim 1 further comprising a binding agent.

29. The synergistic insecticidal composition of claim 28 wherein said binding agent is a pyrrolidine derivative.

30. The synergistic insecticidal composition of claim 1, wherein said composition is in a powder form.

31. The synergistic insecticidal composition of claim 30 wherein said powder form has an average particle size of 2-1500 microns.

32. A process for preparing a synergistic insecticidal composition comprising mixing thoroughly 0.1 to 5% by weight a Chloronicotynyle compound of Imidacloprid, 30 to 75% by weight an Organophosphorus compound of Acephate, said Chloronicotynyle compound and said Organophosphorus compound are the only insecticidally active ingredients, and 69.9 to 20% by weight of at least one agriculturally acceptable compound selected from the group consisting of a conventional agriculturally acceptable carrier and a conventional agriculturally acceptable excipient.

33. The process of claim 32 wherein said at least one agriculturally acceptable compound is selected from the group consisting of mineral earth like silicas, silica gels, silicates, talc, kaolin, montmorillonite, attapulgite, pumice, sepiolite, bentonite, limestone, lime, chalk, clay, dolomite, diatomaceous earth, calcite, calcium sulfate, magnesium sulfate, magnesium sulfate, magnesium oxide, sand, ground plastics, ferilizers like ammonium sulfate, ammonium phosphate, ammonium nitrate, ureas, cereal meal, tree bark meal, wood meal, nutshell meal, and cellulose powders.

34. The process of claim 32 further comprising mixing a surfactant with said Chloronicotynyle compound, said Organophosphorus compound and said at least one agriculturally acceptable compound.

35. The process of claim 34 wherein said surfactant is selected from the group consisting of non-ionic surfactants, cationic surfactants and anionic surfactants.

36. The process of claim 35 wherein said anionic surfactants are selected from the group consisting of alkali metal soaps, alkaline earth metal soaps, substituted or unsubstituted ammonium salts of higher fatty acids, sodium or potassium salt of oleic or stearic acid, and natural fatty acid mixtures.

37. The process of claim 32 further comprising mixing a stabilizer with said Chloronicotynyle compound, said Organophosphorus compound and said at least one agriculturally acceptable compound.

38. The process of claim 37 wherein said stabilizer is selected from the group consisting of ethoxylate of vegetable oil, salts of higher fatty acids, a blend of the derivatives of epoxylated vegetable oil, Ethoxylated polyoxyethylene amine and pyrrolidine, and lactone.

39. The process of claim 32 further comprising mixing a wetting cum dispersing agent with said Chloronicotynyle compound, said Organophosphorus compound and said at least one agriculturally acceptable compound.

40. The process of claim 39 wherein said wetting cum dispersing agent is selected from the group consisting of Alkyl Phenol Ethoxylate, salts of alkyl naphthyl sulphonate, salts of alkyl aryl sulphonate, and derivative of sulfonated fatty alcohol.

41. The process of claim 32 further comprising mixing a wetting agent with said Chloronicotynyle compound, said Organophosphorus compound and said at least one agriculturally acceptable compound.

42. The process of claim 41 wherein the wetting agent is a calcium or sodium salt of alkyl aryl sulphonate.

43. The process of claim 32 further comprising mixing an emetic agent with said Chloronicotynyle compound, said Organophosphorus compound and said at least one agriculturally acceptable compound.

44. The process of claim 43 wherein said emetic agent is a lignocaine derivative or a formulation of lignocaine derivative.

45. The process of claim 32 further comprising mixing an antifoaming agent with said Chloronicotynyle compound, said Organophosphorus compound and said at least one agriculturally acceptable compound.

46. The process of claim 45 wherein said antifoaming agent is a silicone oil derivative.

47. The process of claim 32 further comprising mixing a disintegrating agent with said Chloronicotynyle compound, said Organophosphorus compound and said at least one agriculturally acceptable compound.

48. The process of claim 47 wherein said disintegrating agent used is selected from the group consisting of bentonite clay, Zeolite clay, Attapulgite clay, sodium sulphate salts, and Aluminium sulphate salts.

49. The process of claim 32 further comprising mixing a filler with said Chloronicotynyle compound, said Organophosphorus compound and said at least one agriculturally acceptable compound.

50. The process of claim 49 wherein said filler is selected from the group consisting of silica, kaoline, and clay.

51. The process of claim 32 wherein said agriculturally acceptable compound includes said carrier and said excipient present in a ratio of carrier:excipient in a ratio of 1:1 to 1:10000.

52. The process of claim 32 further comprising mixing an anticaking agent with said Chloronicotynyle compound, said Organophosphorus compound and said at least one agriculturally acceptable compound.

53. The process of claim 52 wherein said anticaking agent is selected from a group consisting of fumed silica, anhydrous Magnesium sulphate, a blend of sucrose and starch derivatives.

54. The process of claim 32 further comprising mixing a dye with said Chloronicotynyle compound, said Organophosphorus compound and said at least one agriculturally acceptable compound.

55. The process of claim 54 wherein said dye is a water soluble dye or a water insoluble dye.

56. The process of claim 32 further comprising mixing a dispersing agent with said Chloronicotynyle compound, said Organophosphorus compound and said at least one agriculturally acceptable compound.

57. The process of claim 56 wherein said dispersing agent is a formaldehyde condensate of alkyl phenols.

58. The process of claim 32 further comprising mixing a binding agent with said Chloronicotynyle compound, said Organophosphorus compound and said at least one agriculturally acceptable compound.

59. The process of claim 58 wherein said binding agent is a pyrrolidine derivative.

60. The process of claim 32 wherein said composition is in the form of a powder.

61. The process of claim 60, wherein said powder has an average particle size of 2-1500 microns.

62. The synergistic insecticidal composition of claim 1, whereby said composition is used to control agricultural pest and hygienic pests.

63. The process of claim 32, whereby said composition is used to control agricultural pests and hygienic pests.

64. The synergistic insecticidal composition of claim 1, whereby said composition is used to protect plants selected from the group consisting of cotton, paddy, rice forage crops, sugarcane, cole crops, leafy vegetables, tobacco, tomatoes, potatoes, flowering ornamentals, vine crops and fruit trees.

65. The process of claim 32, whereby said composition is used to protect plants selected from the group consisting of cotton, paddy, rice forage crops, sugarcane, cole crops, leafy vegetables, tobacco, tomatoes, potatoes, flowering ornamentals, vine crops and fruit trees.

66. The insecticidal composition of claim 1, wherein said composition includes about 1.8 wt. % Imidacloprid.and about 50 wt. % Acephate.

67. The process of claim 32, wherein said composition includes about 1.8 wt. % Imidacloprid.and about 50 wt. % Acephate.

* * * * *